(12) United States Patent
Ehrhardt et al.

(10) Patent No.: US 6,593,511 B1
(45) Date of Patent: Jul. 15, 2003

(54) MODELS OF CHRONIC AND ACUTE INFLAMMATORY DISEASES

(75) Inventors: Rolf Ehrhardt, San Francisco, CA (US); Kenneth Hong, El Cerrito, CA (US)

(73) Assignee: Bioseek, Inc., Burlingame, CA (US)

( * ) Notice: Subject to any disclaimer, the term of this patent is extended or adjusted under 35 U.S.C. 154(b) by 0 days.

(21) Appl. No.: 09/852,448

(22) Filed: May 9, 2001

Related U.S. Application Data
(60) Provisional application No. 60/203,982, filed on May 12, 2000.

(51) Int. Cl.$^7$ ................ A01K 67/00; A01K 67/033; C12Q 1/00; C12Q 5/00; A61K 49/00; A01N 63/00

(52) U.S. Cl. ................ 800/9; 800/8; 800/11; 435/4; 435/375; 424/93.7; 424/9.1; 424/9.2; 424/93.21

(58) Field of Search ............................ 800/3

(56) References Cited

U.S. PATENT DOCUMENTS
5,945,576 A * 8/1999 Parker et al. .................. 800/9

OTHER PUBLICATIONS

Boehneke et al., Pulling the trigger on psoriasis, Feb. 29, 1996, Nature, vol. 379, p. 777.*

Sakaguchi et al., Immunologic Self–Toletance Maintained by Activated T Cells Expressing IL–2 Receptor x–Chains (CD25), 1995, The Journal of Immunology, vol. 155, pp. 1151–1164.*

Gao et al. (Dec. 27, 1999)"CD4+ CD25+ Cells Regulate CD8 Cell Anergy in Neonatal Tolerant Mice." *Transplantation*, vol. 68(12):1891–1897.

Baggiolini, Marco (Apr. 9, 1998), "Chemokines and Leukocyte Traffic." *Nature*, vol. 392:565–568.

Berg et al. (Dec. 1991), "The Cutaneous Lymphocyte Antigen is a Skin Lymphocyte Homing Receptor for the Vascular Lectin Endothelial Cell–Leukocyte adhesion Molecule 1." *J. Exp. Med.* vol. 174:1461–1466.

Berg et al. (1989), "Homing Receptors and Vascular Addressins: Cell Adhesion Molecules that Direst Lymphocyte Traffic." *Immunological Reviews*, No. 108:5–18.

Davidson et al. (1998), "IL–12, But Not IFN–γ, Plays a Major Role in Sustaining the Chronic Phase of Colitis in IL–10–Deficient Mice." *Journal of Immunology*, vol. 161:3143–3149.

Ehrhardt et al. (1997), "Induction and Prevention of Colonic Inflammation in IL–2–Deficient Mice." *Journal of Immunology*, vol. 158:566–573.

Hong et al. (1999), "IL–12, Independently of IFN–γ, Plays a Crucial Role in the Pathogenesis of a Murine PsoriasisLike Skin Disorder." *Vol. Journal of Immunology*, vol. 162:7480–7491.

Itoh et al. (1999), "Thymus and Autoimmunity: Production of $CD25^+$ $CD4^+$ Naturally Anergic and Suppressive T Cells as a Key Function of the Thymus in Maintaining Immunologic Self–Tolerance." *Journal of Immunology*, vol. 162:5317–5326.

Kuhn et al. (Oct. 22, 1993), "Interleukin–10–Deficient Mice Develop Chronic Enterocolitis." *Cell*, vol. 75:263–274.

Mombaerts et al. (Oct. 22, 1993), "Spontaneous Development of Inflammatory Bowel Disease in T Cell Receptor Mutant Mice." *Cell*, vol., 75:275–282.

Neurath et al. (Nov. 1995), "Antibodies to Interleukin 12 Abrogate Established Experimental Colitis in Mice." *Journal of Experimental Medicine*, vol. 182:1281–1290.

Picker et al. (Nov. 1, 1990), "Differential Expression of Homing–Associated Adhesion Molecules by T Cell Subsets in Man." *Journal of Immunology*, vol. 145(10):3247–3255.

Powrie et al. (Jun. 1996), "A Critical Role for Transforming Growth Factor–β but Not Interleukin 4 in the Suppression of T Helper Type–1 mediated Colitis by $CD45Rb^{low}$ $CD4^+$ T Cells." *J. Exp. Med.*, vol. 183:2669–2674.

Powrie et al. (Oct. 1994), "Inhibition of Th 1 Responses Prevents Inflammatory Bowel Disease in scid Mice Reconstituted with $CD45Rb^{hi}$ $CD^{4+}$ T Cells." *Immunity*, vol. 1:553–562.

Sakaguchi et al. (1995), "Immunologic Self Tolerance Maintained by Activated T Cells Expressing IL–2 Receptor α–Chains (CD25)." *Journal of Immunology*, vol. 155:1151–1164..

Shevach et al. (1998), "T Lymphocyte–Mediated Control of Autoimmunity." *Immunology Tolerance*, pp 200–217.

Shimizu et al. (1999), "Induction of Tumor Immunity by Removing $CD25^+$ $CD4^+$ T Cells: A Common Basis Between Tumor Immunity and Autoimmunity." *Journal of Immunology*, vol. 163:5211–5217.

Schon et al. (Feb. 1997), "Murine Psoriasis–Like Disorder Induced by Naïve $CD4^+$ T Cells." *Nature Medicine*, vol. 3(2):183–188.

(List continued on next page.)

*Primary Examiner*—Jeffrey Fredman
*Assistant Examiner*—Jon Angell
(74) *Attorney, Agent, or Firm*—Pamela J. Sherwood; Bozicevic, Field & Francis LLP

(57) ABSTRACT

Methods and compositions are provided for the creation and screening of non-human animal models having chronic inflammation. Immunocompromised host animals are injected with a population of immunocompetent effector cells, depleted of CD25+ T cells. The effector cells are tolerant of the host major histocompatibility antigens, but reactive to at least one antigen present in the host animal. The transferred cells are preferably stimulated and localized by administration of an immunostimulant at a local site. The animals are useful for a variety of screening assays and for investigation into disease causes and pathways. A variety of chronic inflammatory diseases may be studied with this model, including psoriasis, rheumatoid arthritis, diabetes, inflammatory bowel disease and multiple sclerosis.

12 Claims, 9 Drawing Sheets

OTHER PUBLICATIONS

Suri–Payer et al. (1998), "CD4+ CD25+ T Cells Inhibit Both the Induction and Effector Function of Autoreactive T Cells and Represent a Unique Lineage of Immunoregulatory Cells." *Journal of Immunology*, vol. 160:1212–1218.

Takahashi et al. (1998), "Immunologic Self–Tolerance Maintained by CD25+ CD4+ Naturally Anergic and Suppressive T Cells: Induction of Autoimmune Disease by Breaking their Anergic/Suppressive State." *International Immunology*, vol. 10(12):1969–1980.

Tarrant et al. (1998), "Endogenous IL–12 is Required for Induction and Expression of Experimental Autoimmune Uveitis." *Journal of Immunology*, vol. 161:122–127.

Von Adrian et al. (Sep. 1991), "Two–Step Model for Leukocyte–Endothelial Cell Interaction in Inflammation: Distinct Roles for LECAM–1 and the Leukocyte $\beta 2$ Integrins in vivo." *Proc. Natl. Acad. Sci. USA*, vol. 88:7538–7542.

\* cited by examiner

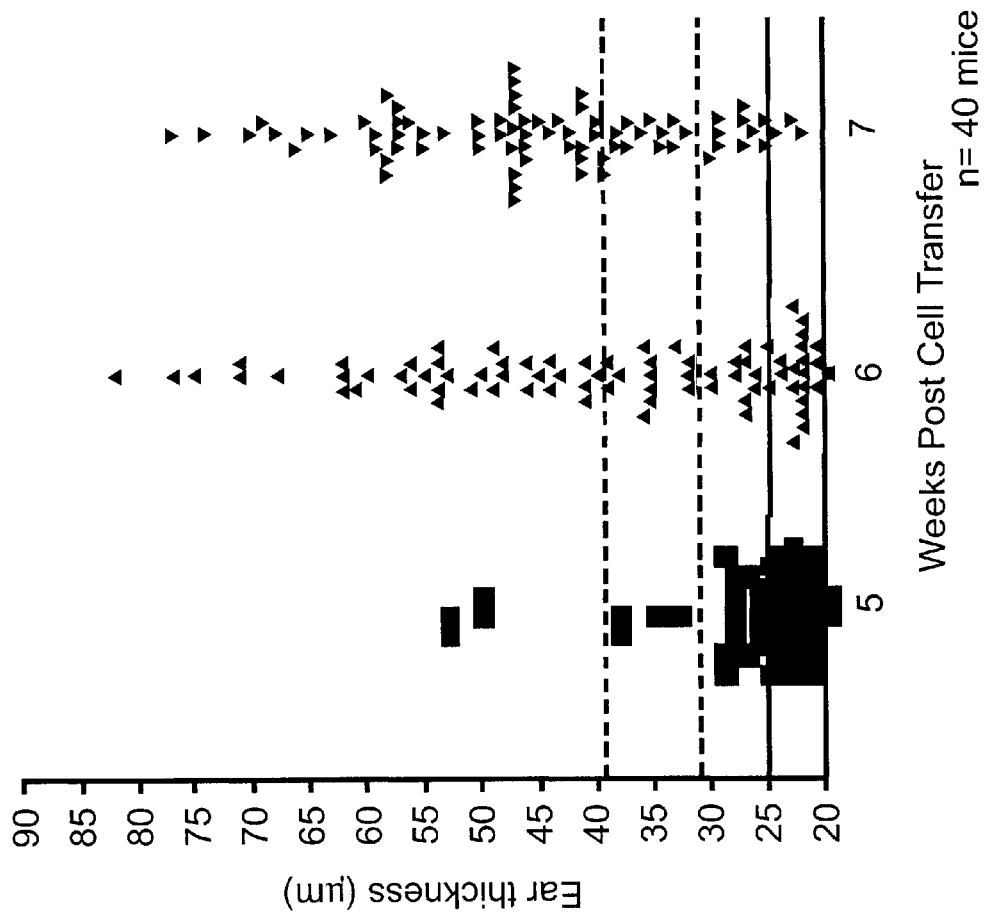

FIG. 10

Bar chart: Incidence of Moderate to Severe Disease (%)

- no Coinj: 0%
- LPS: 20%
- LPS + Whole Cells: 20%
- Viral Vector: 40%
- SEB: 0%

MODELS OF CHRONIC AND ACUTE INFLAMMATORY DISEASES

BACKGROUND OF THE INVENTION

Despite recent advances in genomic sequencing efforts, as well as in the fields of pre-clinical drug screening/development and clinical trial design, the transfer of existing "pre-clinical" knowledge into the clinic is still very difficult. This is mainly due to the sparse knowledge of the events that occur during the initiation, the perpetuation and the maintenance of inflammatory disease states in humans.

The reasons for such incomplete and often low quality information are numerous: humans cannot intentionally be studied in the pre-clinical phase, cell isolation is difficult from human tissue, the starting events of an autoimmune reaction occur without notice, and patients with autoimmune or other inflammatory diseases may not wish to be treated as experimental subjects. As a result, there is a lack of reliable information on which to base decisions about clinical trials. When clinical symptoms arise and treatment is required, rational selection from among the many potential anti-inflammatory compounds or combinations thereof is difficult.

In order to identify new and useful drugs, screening assays must be able to provide biologically relevant information, so that there is a good correlation between the information generated by the screening assay and the pharmaceutical effectiveness of the compound. Some of the more important features for pharmaceutical effectiveness are specificity for the targeted cell or disease, a lack of toxicity at relevant dosages, and specific activity of the compound against its molecular or cellular target.

Inflammatory conditions, particularly chronic inflammatory diseases, are of particular interest. These diseases are caused by the action of the immune system, including the inappropriate activation of T cells, expression of regulatory cytokines and chemokines, loss of immune tolerance, and the like. Modulation of the immune response varies with the specific factors produced, and the receptors present on the responding cell.

Among these diseases are autoimmune and/or chronic inflammatory diseases, which include multiple sclerosis and inflammatory bowel diseases (IBD, ulcerative colitis and Crohn's disease), colitis, diseases of the joints, such as rheumatoid arthritis, attacks on nucleic acids, as observed with systemic lupus erythematosus and such other diseases as psoriasis, insulin dependent diabetes mellitus (IDDM), Sjogren's disease, myasthenia gravis, thyroid disease, Alzheimer disease, uveitis, and cardiovascular diseases.

The initiating step in autoimmune disease pathology is still mysterious in many cases, particularly in humans where the diseases are largely sporadic, and symptoms may appear years after the first T cell launches its attack. It has therefore been difficult to design effective therapies that prevent initiation of disease, although there are common features in many of the later stages of disease. Inflammation at the site of the disease is often found, caused by the release of inflammatory cytokines by T cells and other pro-inflammatory cells (e.g. macrophages, dendritic cells, B cells, NK cells), and accompanied by the destruction of autologous cells.

Recent studies using murine models of experimental chronic inflammation are defining the nature of the immunological disturbances that initiate inflammation and destruction of specific organs (for example, see Mombaerts et al. Cell, 1993. 75(2): p. 274–82; Tarrant et al. J Immunol, 1998. 161(1): p. 122–7; Powrie et al. Immunity, 1994. 1: p. 553–562; Hong et al. J Immunol, 1999. 162(12): p. 7480–91; Horak, Clin Immunol Immunopathol, 1995. 76(3 Pt 2): p. S172–3; Ehrhardt et al. J Immunol, 1997. 158(2): p. 566–73; Davidson et al., J Immunol, 1998. 161(6): p. 3143–9; Kuhn et al. Cell, 1993. 75(2): p. 263–74; Neurath et al., J Exp Med, 1995. 182(5): p. 1281–90). Increased understanding of disease promoting inflammatory cells is providing insights into the mechanism controlling the immune responses within target organs.

Evidence has been presented in the literature for the involvement of different T cell subsets in the development of disease. An important role for a distinct T cell population including regulatory and/or suppressor T cells in maintaining the physical integrity of organ specific immunity has been suggested by recent several studies (Suri-Payer et al., J Immunol, 1998. 160(3): p. 1212–8; Shevach et al., Novartis Found Symp, 1998. 215: p. 200–11). These investigators and others (Shimizu et al., J Immunol, 1999. 163(10): p. 5211–8; Itoh et al., J Immunol, 1999. 162(9): p. 5317–26; Sakaguchi et al J Immunol, 1995. 155(3): p. 1151–64; Takahashi et al., Int Immunol, 1998. 10(12): p. 1969–80) have postulated that CD4+ CD25+ T cells play a crucial role in the suppression of immune responses and one might postulate if a cell population is transferred into an immunodeficient mouse without its suppressor CD25+ subset, autoimmunity can occur at multiple sites of the body. This presumes of course that autoimmune causing effector cells are able to reach their target organ. Such an effector cell permissive environment is probably created through the upregulation of adhesion molecules (Berg et al., Immunol Rev, 1989. 108: p. 5–18; von Andrian et al., Proc Natl Acad Sci USA, 1991. 88(17): p. 7538–42; Berg et al., J Exp Med, 1991. 174(6): p. 1461–6; Picker et al. J Immunol, 1990. 145(10): p. 3247–55) and the secretion of chemokines (Baggiolini, Nature, 1998. 392(6676): p. 565–8) on the affected tissues, and on endothelial cells allowing the entrance and retention of effector cells into the tissue.

To study the regulatory effects of T cells and other immunocompetent cells, animal models have provided a very good tool in the past. An essential role for the study of human autoimmune conditions was played in particular by the scid/scid CD4+CD45Rb$^{hi}$ cell transfer model. Over the last decade this model has proven to be a viable scientific tool for the study of dysregulated immune responses, and moreover, has been proven to be a good tool for the discovery and evaluation of treatment/drug targets, candidates for inflammatory bowel disease and recently psoriasis (Hong et al., supra.; Powrie et al., J Exp Med, 1996. 183(6): p. 2669–74; Schon et al., Nat Med, 1997. 3(2): p. 183–8). Notably, not only do these animal models resemble human histology and physiology in some ways or another, but have been helpful in determining novel treatment strategies in humans for both diseases.

One major disadvantage of conventional animal models is that they are very labor-intensive and costly and thus do not permit large throughput drug screening. Unfortunately, in vitro screening techniques are limited in their predictive power. Thus, despite today's advances in pre-clinical science, hard decisions must be made without complete pre-clinical, in vivo data.

With drug discovery moving from target identification to validations, reliable biological systems are necessary to confirm, validate and support the recent explosion in the number of potential new drug targets and drug compounds. The development of robust, reproducible and scaleable animal models that physiologically resemble human disease is very desirable; i.e. models in which the inflammation is truly chronic in nature and the histology that of human, and can be used as treatment models and not only preventive ones. Such animal models must posses the utility to rapidly advance experimental drug leads rapidly and reliably in a semi- to high through-put fashion, leading to novel, effective and safe therapeutics.

SUMMARY OF THE INVENTION

Models are provided for chronic inflammatory diseases. The models are useful for testing and screening of biologically active agents for the treatment of chronic and acute inflammatory disease. A cell population comprising immunocompetent effector cells, which lacks $CD25^+$ suppressor T cells, is transferred into a cellular environment that lacks $CD25^+$ suppressor T cells but contains a T cell antigen. Preferably, an immunostimulant and/or immunomodulatory co-factor and/or T cell antigen is introduced at a targeted site or organ after the T cell introduction to enhance T cell response and homing. Animals develop acute and chronic inflammatory responses at the targeted site, and provide a useful model for the development of inflammation, and for drug/gene screening in the prevention and treatment of chronic inflammatory disease in humans.

BRIEF DESCRIPTION OF THE DRAWINGS

FIG. 1 is a graph depicting disease penetration.

FIG. 10 shows the effect of different co-factors on disease induction.

DESCRIPTION OF THE SPECIFIC EMBODIMENTS

Figure 2A:
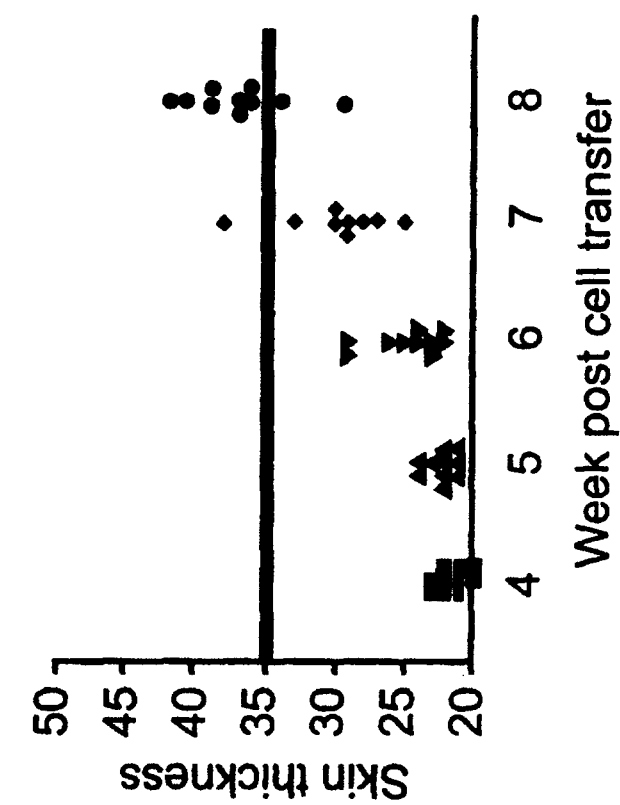
FIGS. 2A and 2B are graphs depicting the disease scalability and distribution. Each symbol represents a single ear measurement. (n=10).

Non-human animal models for chronic inflammatory disease are provided. The animals are particularly suited as models for T cell mediated autoimmune diseases, such as multiple sclerosis, insulin dependent diabetes mellitus, rheumatoid arthritis, and the like.

An immunocompromised host animal is injected with a population of immune cells depleted of $CD25^+$ cells, from a donor animal of the same or related species. The transferred cells may comprise T cells, natural killer (NK) cells, monocytes, etc. The cell population may be further selected to enrich for T cell types of interest. For example, the cells may be selected to have the phenotype $CD4^+CD25^-$. The $CD25^+$ population contains suppressive T cells that act to down-regulate the T cell response. By transferring a population of $CD25^-$ cells, the immune responsiveness of the cells is increased.

The host and donor animals are matched, and/or tolerant at the host major histocompatibility antigens, e.g., are of the same MHC haplotype (MHC matched) but the transferred T cells are responsive to at least one antigen present in the recipient, e.g. are mismatched at one or more minor antigens, or otherwise responsive to the presence of a T cell antigen. For example, a mismatch at minor histocompatibility loci provides the antigenic immune stimulation for development of chronic inflammation. In a preferred embodiment, an immunostimulant/modulatory co-factor is administered at a targeted site, in order to localize the effector T cells.

These animals provide a useful model for the specific pathogenic requirements of Th1 promoting cytokines and cells. By providing a more accurate model for the human disease, potential therapeutics can be evaluated in the animal model for safety and efficacy prior to clinical trials. In addition to screening candidate pharmaceutical agents, the subject animals are useful in determining the role of "triggering" agents in development of disease, the role of specific T cell subsets and cytokines, and the role of specific antigens in activation and maintenance of inflammatory T cells.

Immunocompromised mammalian hosts suitable for implantation and having the desired immune incapacity exist or can be created. The significant factor is that the immunocompromised host is incapable of mounting an immune response against the introduced pathogenic effector T cells. Preferred host animals will lack CD25+ T cells. Of particular interest are small mammals, e.g. rabbits, gerbils, hamsters, guinea pigs, etc., particularly rodents, e.g. mouse and rat, which are immunocompromised due to a genetic defect that results in an inability to undergo germline DNA rearrangement at the loci encoding immunoglobulins and T-cell antigen receptors or to a genetic defect in thymus development (nu/nu).

Presently available hosts include mice that have been genetically engineered by transgenic disruption to lack the recombinase function associated with RAG-1 and/or RAG-2 (e.g. commercially available TIM™ RAG-2 transgenic), to lack Class I and/or Class II MHC antigens (e.g. the commercially available C1D and C2D transgenic strains), or to lack expression of the Bcl-2 proto-oncogene. Of particular interest are mice that have a homozygous mutation at the scid locus, causing a severe combined immunodeficiency which is manifested by a lack of functionally recombined immunoglobulin and T-cell receptor genes. The scid/scid mutation is available or may be bred into a number of different genetic backgrounds, e.g. CB.17, ICR (outbred), C3H, BALB/c, C57Bl/6, AKR, BA, B10, 129, etc. Other mice which are useful as recipients are NOD scid/scid; SGB scid/scid, bh/bh; CB.17 scid/hr; NIH-3 bg/nu/xid and META nu/nu. Transgenic mice, rats and pigs are available which lack functional B cells and T cells due to a homozygous disruption in the $CD3_\epsilon$ gene. Immunocompromised rats include HsdHan:RNU-rnu; HsdHan:RNU-rnu/+; HsdHan:NZNU-rnu; HsdHan:NZNU-rnu/+; LEW/HanHsd-rnu; LEW/HanHsd-rnu/+; WAG/HanHsd-rnu and WAG/HanHsd-rnu/+.

Generally, the host will be at least about four weeks old. For example, mice are often used at about 4 to 12 weeks of age. The mammalian host will be grown in conventional ways. Depending on the degree of immunocompromised status of the mammalian host, it may be protected to varying degrees from infection. An aseptic environment is indicated. Prophylactic antibiosis may be used for protection from infection. Alternatively, it may be satisfactory to isolate the potential hosts from other animals in gnotobiotic environments after cesarean derivation. The feeding and maintenance of the host will for the most part follow gnotobiotic techniques.

The major histocompatibility locus haplotype of the host animal is determined either through conventional typing methods, e.g. where outbred animals are used, or from known information concerning the genetic characteristics of the animal. In mice, the genes of the major histocompatibility locus (MHC) have been very well characterized. The MHC region is comprised of a number of genes, of which at least five contribute to acute graft rejection and graft vs. host disease. The specific MHC genes of interest include the class I antigens: H2-K, H2-D, and H2-L; and the class II antigens: H2 I region, which includes H2-Aa, Ab, Bl, Ea, Eb, Eb2, Ob, and Pb. Specific information on the haplotype of most known mouse strains may be found in Klein et al. (1983) *Immunogenetics* 17(6):553–96.

The immunocompromised host animals are injected with a cell population comprising immunocompetent T cells, and lacking $CD25^+$ cells. Conveniently, a cell population is depleted by reagents specific for CD25 (negative selection), e.g. anti-CD25 antibodies, by flow cytometry, magnetic bead depletion, etc. Alternatively, T cell populations naturally deficient in CD25 expression, or deficient through gene targeting from CD25 knockout mice may be used.

The T cells may be from an allogeneic or xenogeneic donor, and are tolerant to the major histocompatibility antigens of the recipient, but immunoreactive with an antigen present in the recipient, e.g. a T cell antigen provided by viral infection of the recipient, chronic infection with a bacterial or protozoan pathogen, sustained release of an antigenic compound, the presence of one or more minor histocompatibility antigens of the recipient, etc. By tolerant is meant that when mixed with appropriate cells (e.g., irradiated lymphocytes) from the recipient, the donor T cells proliferate to a substantially lesser extent (e.g., <about 10% to 25%) than in an analogous mixed lymphocyte reaction between MHC mismatched cells.

In contrast to the MHC locus, there are many minor histocompatibility antigen loci dispersed throughout the genome. Minor antigens generally result from the presentation of cellular proteins on the surface of cells in conjunction with self MHC. Therefore, virtually any protein that is expressed by the host, processed and presented in the context of MHC antigens, and is polymorphic between host and donor, can serve as a minor histocompatibility antigen. Where there is a persistent or chronic infection, epitopes relating to the infectious agent can serve as minor histocompatibility antigens. It has been suggested that some cutaneous antigens may serve as a trigger for chronic inflammatory disease (e.g. H-40, described by Forman et al. (1984) *J. Exp. Med.* 159:1724–1740; and other antigens described by Chang et al. (1994) *P.N.A.S.* 91:9282–9286; or Menssen et al. (1995) *J. Immunol.* 155:4078–4083). The subject animals are valuable models for determining the role of specific genetic loci in contributing to the development of inflammatory disease. Such screening may utilize animals that are mismatched only at the loci of interest, and then determining whether the difference is sufficient for induction of disease.

There are a number of suitable animals to use as the source of T cells. In most cases the donor and recipient will be of the same species, although for some purposes xenogeneic donors may be used. In one embodiment of the invention, the donor is allogeneic but is matched at the MHC locus. For example, congenic mouse and rat strains are available that are isogenic at the MHC locus, but have a different genetic background. Alternatively, a parental strain may be used as a donor, while an F1 animal acts as recipient, e.g. a BALB/c donor into a BALB/c×C57bl/6 recipient. Alternatively, syngenic cells can be used in the presence of other exogenous T cell antigen(s) in the host environment, e.g. proteins, peptides, endotoxins, superantigens, and the like. Alternatively, CB57/BL6 mice can be used as donors, and the donor cells can be transferred into RAG-1™ and/or RAG-2™ deficient mice.

Alternatively, one may use a chimeric animal as the source of donor cells. For example, one can create a chimera by transferring hematopoietic stem cells (HSC) into a recipient, where the HSC are of a different genotype than the recipient. The HSC then differentiate into T cells which are "educated" in the thymus, and so are restricted to the recipient MHC type. These cells from the chimera can then be harvested and used in the subject methods, because they are both tolerant and restricted to the MHC type of the thymus. It will be understood by one of skill in the art that the thymic MHC in this example must be compatible with the ultimate recipient animal. This procedure can also be used to create xenogeneic chimeras (see for example, U.S. Pat. No. 5,625,127), allowing the use of human cells in the subject methods.

The injected cell population comprises immunocompetent T cells, and may also comprise other CD25 negative hematopoietic cells, including macrophages, B cells, monocytes, etc. T cells are conveniently isolated from secondary immune organs, e.g. spleen, lymph node, thymus, etc. For example, an unfractionated suspension of spleen cells, lymph node, etc. can be depleted of $CD25^+$ cells and injected into the animal. Cells may also be isolated from peripheral blood, cord blood, apheresis product, etc. Cell populations may be enriched for various cell fractions of interest, e.g. by density gradient, elutriation, cell sorting, etc. In one embodiment of the invention, the population is selected for CD4 positive cells, which enriches for T helper cells. In another embodiment of the invention, the cell population is depleted of hematopoietic and lymphoid progenitor cells, as known in the art, in order to decrease the possibility of de novo T cell maturation in the host animal.

In another embodiment, the CD25 depleted cell population is pre-incubated with antigen presenting cells, which may be syngeneic, allogeneic, xenogeneic, usually comprising an exogenous antigen to which the CD25 depleted population is responsive; having mismatches at minor MHC loci; and the like. Optionally, pro-inflammatory factors, e.g. lymphokines, endotoxins, superantigens etc.; or antibodies against suppressor factors, e.g. TGF-$\beta$ or IL-10, etc. are present. The cells are incubated for a period of time sufficient to induce an immune response, and are then introduced into a normal non-immunocompromised or immunocompromised host. In another embodiment, whole cells are incubated with pro-inflammatory cytokines that down-regulate CD25 expression on T cells and then are introduced into the host environment, e.g. non-immunocompromised or immunocompromised, syngenic or minor-haplotype mismatched.

Inflammatory diseases can also be transferred from one animal expressing disease to another naive animal by extracting effector cells from the diseased animal and injecting them into multiple naive animals. In another embodiment, a secondary transfer is performed, where whole spleen or lymph node cells from a primary host that was previously treated with a CD25 depleted population, as described above, are transferred into a secondary host. The primary host may be diseased or not-diseased. The cells from the primary host may be unfractionated spleen, lymph node, etc., or may be depleted of CD25 positive cells. Effector cells can be found in secondary lymphoid tissue, especially spleen but also draining lymph node, and the actual diseased organ tissue.

Separation of the desired cells for engraftment will generally use affinity separation to provide a substantially CD25 negative population, usually comprising after separation not more than about 5% CD25$^+$ cells, more usually not more than about 3% CD25$^+$ cells, and may be less than about 1% CD25$^+$ cells. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, LDS). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; ligand and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding agents are well-known to those skilled in the art.

Of particular interest is the use of antibodies as affinity reagents. Conveniently, these antibodies are conjugated with a label for use in separation or used in conjunction with a labeled second antibody that binds to them. Labels include magnetic beads, which allow for direct separation; biotin, which can be bound to avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red.

The antibodies are added to a suspension of lymphocytes, and incubated for a period of time sufficient to bind the available cell surface antigens. The incubation will usually be at least about 5 minutes and usually less than about 30 minutes. It is desirable to have a sufficient concentration of antibodies in the reaction mixture so that the efficiency of the separation is not limited by lack of antibody. The appropriate concentration is determined by titration. The medium in which the cells are separated will be any medium which maintains the viability of the cells and binding of antibody. A preferred medium is phosphate buffered saline containing from 0.1 to 0.5% BSA. Various media are commercially available and may be used according to the nature of the cells, including Dulbecco's Modified Eagle Medium (DMEM), Hank's Basic Salt Solution (HBSS), Dulbecco's phosphate buffered saline (DPBS), RPMI, Iscove's medium, PBS with 5 mM EDTA, etc., frequently supplemented with fetal calf serum, BSA, HSA, etc.

The labeled cells are then separated as to the expression of CD25, and optionally CD4. The separated cells may be collected in any appropriate medium that maintains the viability of the cells, usually having a cushion of serum at the bottom of the collection tube. Various media are commercially available and may be used according to the nature of the cells, including DMEM, HBSS, DPBS, RPMI, Iscove's medium, etc., frequently supplemented with fetal calf serum.

Compositions enriched for the desired T cells are achieved in this manner. 90% of CD25pos T cells are depleted in the final CD25negative T cell population. The enriched cell population may be used immediately, or may be frozen at liquid nitrogen temperatures and stored for long periods of time, being thawed for use when needed. The frozen cells will usually be stored in 10% DMSO, 10–90% FCS, 40% RPMI 1640 or other medium. Once thawed, the cells may optionally be expanded by use of growth factors or stromal cells associated with T cell proliferation and differentiation.

The population of purified T cells are injected into the immunocompromised recipient. Routes of administration include systemic injection, e.g. intravascular, subcutaneous, or intraperitoneal injection. Where the recipient animal is a mouse, the number of cells injected will usually be at least about $0.5 \times 10^5$ and not more than about $5 \times 10^5$, more usually at least about $1 \times 10^5$, preferably between about $3 \times 10^5$ and $4 \times 10^5$. Where the recipient animal is a larger animal, the number of cells will be increased accordingly.

Preferably, after transfer of the T cell population, a localized immunostimulant and/or immunomodulating co-factor is delivered in order to facilitate localization, retention and replication of the effector, disease causing T cells. An immunostimulant or immunomodulator can be any agent that can contribute or induce either directly or indirectly inflammation through the release of cytokines, lymphokines and the upregulation of adhesion molecules. To accomplish this, the co-factor is administered, generally at a localized site, following transfer of the T cells. The timing of administration is varied depending on the desired effect, but is generally performed from 1 day to 1 week after T cell transfer. Many immunostimulants are known in the art, including LPS and endotoxins in small doses, alpha interferons, interleukin-1, modified tumor necrosis factor, CD40 ligand, poly IC, virus, etc.

In one embodiment of the invention, the immunostimulatory co-factor is a virus or viral vector, e.g. adenovirus, vaccinia, HSV, SV40, and AAV, etc. The immunostimulatory effect may be provided by the viral coat proteins present on the virus particles, and/or by viral proteins or other genes expressed upon infection of the target cell. Live virus is not required for the co-factor effect, killed virus or vector encoding viral proteins are also suitable. Suitable systems are disclosed, for example, in Fisher-Hoch et al., PNAS 86:317–321, 1989; Flexner et al., Ann. N.Y. Acad. Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616–627, 1988; Rosenfeld et al., Science 252:431–434, 1991; Kolls et al., PNAS 91:215–219, 1994; Kass-Eisler et al., PNAS 90:11498–11502, 1993; Guzman et al., Circulation 88:2838–2848, 1993; and Guzman et al., Cir. Res. 73:1202–1207, 1993. Techniques for incorporating DNA into such expression systems are well known to those of ordinary skill in the art. The DNA may also be "naked," as described, for example, in published PCT application WO 90/11092, and Ulmer et al., Science 259:1745–1749, 1993. The uptake of naked DNA may be increased by coating the DNA onto biodegradable beads, which are efficiently transported into the cells. In addition to viral genes, vectors and viruses can be modified to encode immunomodulatory genes, e.g. IL-2, IL-12, CD40, IFN-gamma, GM-CSF, TNF-alpha, etc.

The immunostimulant is administered to the host in the manner conventional for the particular composition, generally as a single unit dose in buffered saline, optionally combined with an adjuvant formulation, where booster doses, typically one to several weeks later, may additionally be delivered enterally or parenterally, e.g., subcutaneously, cutaneously, intramuscularly, intradermally, intravenously, intraarterially, intraperitoneally, intranasally, orally, intraheart, intrapancreas, intraarticular, etc. Localization can be achieved by administration at the targeted site, use of sustained release implants, delivery in the form of non-diffusible particles, and the like, as known in the art.

In one embodiment of the invention, the immunostimulant is a polyclonal activating agent, which may include endotoxins, e.g. lipopolysaccharide (LPS); and superantigens (exotoxins) (see Herman et al. (1991) *Annu Rev Immunol* 9:745–72). Endotoxin primarily interacts with CD14 receptors on macrophages, while superantigens preferentially activate T cells. Both cell types are thus triggered to release pro-inflammatory cytokines. Superantigens (SAgs) are presented by major histocompatibility complex (MHC) class II molecules and interact with a large number of T cells expressing specific T cell receptor V beta domains. SAgs may be endogenous, e.g. Mls; bacterial, e.g. SEB, SEA; or viral, e.g. mouse mammary tumour virus.

Alternatively, one may use immunostimulatory polynucleotide sequences (ISS). The use of these sequences is known in the art, for examples see Bauer et al. (1999) *Immunology* 97(4):699–705; Klinman et al. (1999) *Vaccine* 17(1):19–25; Hasan et al. (1999) *J Immunol Methods* 229 (1–2):1–22; and others. For example, an "immunostimulatory oligonucleotide" has been described as an oligonucleotide that contains a cytosine/guanine dinucleotide sequence and stimulates maturation and activation of DC. An immunostimulatory oligonucleotide of interest may be between 2 to 100 base pairs in size and typically contain a consensus mitogenic CpG motif represented by the formula: 5' $X_1 X_2$ $CGX_3 X_4$ 3', where C and G are unmethylated, $X_1, X_2, X_3$ and $X_4$ are nucleotides and a GCG trinucleotide sequence is not present at or near the 5' and 3' termini (see U.S. Pat. No. 6,008,200, Krieg et al., issued Dec. 28, 1999, herein incorporated by reference).

Preferably the immunostimulatory oligonucleotides range between 8 to 40 base pairs in size. In addition, the immunostimulatory oligonucleotides are preferably stabilized oligonucleotides, particularly preferred are phosphorothioate stabilized oligonucleotides. In one embodiment, $X_1 X_2$ is the dinucleotide GpA. In another embodiment, $X_3 X_4$ is the dinucleotide TpC or TpT.

The dose and protocol for delivery of the immunostimulant will vary with the specific agent that is selected. Typically one or more doses are administered. One particular advantage of the use of ISS in the methods of the invention is that ISS exert immunomodulatory activity even at relatively low dosages. Although the dosage used will vary depending on the clinical goals to be achieved, a suitable dosage range is one which provides from about 1 Fg to about 10,000 Fg, usually at least about 1,000 Fg of ISS in a single dosage. Alternatively, a target dosage of ISS can be considered to be about 1–10 femtomole in a sample of host blood drawn within the first 24–48 hours after administration of ISS. Based on current studies, ISS are believed to have little or no toxicity at these dosage levels.

In an alternative embodiment, a non-replicating virus or viral coat protein is used as the immunostimulant. Virions of interest include herpes viruses, e.g. HSV, EBV, CMV, etc.; adenoviruses, e.g. E1 deleted adenovirus; retroviruses; etc. The virus may optionally comprise a marker gene, such as lacZ, in order to track efficiency of infection. For examples, see Byrnes et al. (1995) *Neuroscience* 66(4):1015–24; Wood et al. (1994) *Gene Ther* 1(5):283–91; and Kajiwara et al. (1997) *Hum Gene Ther* 8(3):253–65.

Injection of a non-replicating virus leads to an inflammatory response, e.g. in brain or neural tissue. Much of this inflammation is induced directly by the virion particles themselves rather than through the expression of new proteins from the virus. By two days there is a large increase in major histocompatibility complex class I and P-selectin expression and a heavy infiltration of leukocytes, mainly macrophages and T cells.

In an alternative embodiment, the CD25 depleted cells are introduced into a pro-inflammatory environment either before or during in vivo introduction to the host. A pro-inflammatory environment can be induced by adding pro-inflammatory factors or antibodies against anti-inflammatory (suppressor) factors, e.g. IFN-γ, IL-12, TNF-alpha, anti-TGF-beta, anti-IL-10, in vivo and/or in vitro prior to introduction into an animal.

After administration of the T cells and co-factor, within about 4 to 8 weeks the animals develop chronic inflammatory disease. Scoring of the disease severity is based on physical appearance, measurable ear thickness, cytokine expression, presence of T cells at the lesion, etc. A more detailed analysis may utilize histological section of various tissues, conveniently ear, eyelid, tail, etc. Specific histological features include mononuclear cell infiltration; high vascular density; etc.

To more fully characterize the disease, immunophenotypic analysis may be performed to detect a variety of relevant antigenic determinants. To characterize the types of immune cells present, immunohistochemical stains for various leukocyte markers may be performed. The expression of additional adhesion molecules that are relevant to the pathophysiology of chronic inflammatory disease may include mononuclear cell infiltrate; T cells at lesions; and the expression in adjacent blood vessels of focal E-selectin, P-selectin, ICAM-1 and diffuse vascular cell adhesion molecule-1 (VCAM-1) expression.

The subject animals are useful for screening candidate therapeutic agents and treatment modalities. Through use of the subject animals or cells derived therefrom, one can identify ligands or substrates that affect the progression of chronic inflammatory disease. Of particular interest are screening assays for agents that have a low toxicity for human cells.

Drug screening protocols will generally include a panel of animals, for example a test compound or combination of test compounds, and negative and/or positive controls, where the positive controls may be known immunosuppressive agents. Such panels may be treated in parallel, or the results of a screening assay may be compared to a reference database.

A wide variety of assays may be used for this purpose, including histological analysis of effectiveness, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cells derived therefrom, particularly skin cells, e.g. keratinocytes. Cells may be freshly isolated from an animal, or may be immortalized in culture. Candidate therapies may be novel, or modifications of existing treatment options.

For screening assays that use whole animals, a candidate agent or treatment is applied to the subject animals. Typically, a group of animals is used as a negative, untreated or placebo-treated control, and a test group is treated with the candidate therapy. Generally a plurality of assays are run in parallel with different agent dose levels to obtain a differential response to the various dosages. The dosages and routes of administration are determined by the specific compound or treatment to be tested, and will depend on the specific formulation, stability of the candidate agent, response of the animal, etc.

The analysis may be directed towards determining effectiveness in prevention of disease induction, where the treatment is administered before induction of the disease, i.e. prior to injection of the T cells and/or pro-inflammatory cytokine. Alternatively, the analysis is directed toward regression of existing lesions, and the treatment is administered after initial onset of the disease, or establishment of moderate to severe disease. Frequently, treatment effective for prevention is also effective in regressing the disease.

In either case, after a period of time sufficient for the development or regression of the disease, the animals are assessed for impact of the treatment, by visual, histological, immunohistological, and other assays suitable for determining effectiveness of the treatment. The results may be expressed on a semi-quantitative or quantitative scale in order to provide a basis for statistical analysis of the results.

The term "agent" as used herein describes any molecule, e.g. protein or pharmaceutical, with the capability of affecting the severity of chronic inflammatory disease. An agent or treatment, e.g. UV light, is administered to an animal of the invention, or to cells derived therefrom. Antibodies specific for cytokines, polyclonal activating agents, and T cell antigens are agents of particular interest. Most preferably, according to another aspect of the instant invention, the agents are monoclonal antibodies, e.g. which neutralize lymphokines or block adhesion molecules.

Other candidate agents encompass numerous chemical classes, typically organic molecules. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The therapeutic agents may be administered to patients in a variety of ways, orally, topically, parenterally e.g. subcutaneously, intramuscularly, intravascularly, etc. Depending upon the manner of introduction, the compounds may be formulated in a variety of ways. The concentration of therapeutically active agent in the formulated pharmaceutical compositions may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a mouse" includes a plurality of such mice and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Animal Model for Chronic Inflammation

Mice. Female Balb/c mice (donor mice) were purchased from Jackson Labs (Bar Harbor, Me.) or similar source, and C.B-17/Icr scid/scid (recipient mice) were purchased from Taconic (Germantown, N.Y.) or Charles River. All mice were housed in a specific pathogen free environment and were used between 4–8 wk of age. Mice were housed 2–5 per microisolator. All scid/scid mice were handled with gloves under a class II hood, fed sterile food and water ad libitum, and maintained in sterilized microisolators that are changed twice weekly. Donor mice were housed in conventional cages that were changed weekly.

Induction of chronic skin inflammation. Briefly, splenocytes were collected from 5–10 week old donor mice (Balb/c) and donor population was either enriched for CD4+ and depleted of CD25+ cells, or depleted of CD25+ cells only. The collected cell population was injected subcutaneously (s.c.) into C.B-17/Icr scid/scid mice, aged 4–8 weeks (usually $3\times10^5$ to $5\times10^5$ cells per mouse in 200–400 $\mu$L). A systemic (s.c., i.p. or i.v.) injection of an immunomodulating agent was given 24 hours following cell transfer. Alternatively, these co-injections were given at the same time to one week after. The co-injection was, alternatively, repeated every other day or once a week for the entire course of the experiment.

Day 0:

Cell Selection: Balb/c mouse spleens were collected and homogenized by pressing through 100 $\mu$ cell strainer (Falcon) and suspended in cold PBS supplemented with 10% FBS. Cell suspension was then centrifuged (400G) and the cell pellet was retained, resuspended in 2 ml warm RBC lysing buffer (37C) per spleen, and incubated 3 minutes at 37° C. The cells were then washed with cold PBS+10% FBS and again centrifuged. The cell pellet was then resuspended in 5 ml cold PBS+10% FBS and we added CD4+ selection beads (Dynal) 251 $\mu$l per spleen to the cell suspension. This mixture was then incubated for 30 minutes at 4° C. on a rotator and using a magnetic particle collector (MPC) the bead-cell complexes were collected and rinsed three times with PBS+10% FCS. The cell-bead complexes were then resuspended in 5 ml warm media (DME, RPMI)+10% FBS, and 20 $\mu$l/spleen CD4 DetachaBead (Dynal) was added and incubated for 45 minutes RT on rotator to remove beads from the cell surface. We removed beads using a MPC, rinsed them twice with PBS+10% FBS and retained supernatants. The resultant cell quantities were 5–8 million cells per spleen. We then resuspend these cells in 1 ml PBS+10% FBS with 8 $\mu$l/spleen anti-CD25-Biotin conjugated mAb and incubate 20 minutes 4° C. Again, cells were washed and resuspended in 1 mL PBS+10% FBS with 25–30 $\mu$l steptavidin beads and incubate for 20 minutes at 4° C. Bead-CD25+ cell complexes were removed using an MPC. The cells were once again, collected, washed, and the pellet was checked for stray beads which were removed if necessary using MPC.

Scid/scid mice were then injected with $1\times10^5$–$5\times10^6$ cells in 200–400 $\mu$l PBS sc. (all SC injections were done with the mice under general anesthesia).

After 24 hours all recipient mice were given a co-injection of 20 $\mu$g LPS (or 10 $\mu$g SEB) s.c. Disease causing T cells then proliferated and began to induce inflammation over a period of 4 weeks Week 4–6: Disease expression period. Beginning on week 4, measurements of skin thickness were taken from both ears to monitor level of disease expression and incidence.

The thickness of the skin on the ear was measured using a Dyer micrometer. The micrometer was first modified to better perform in the measurement of soft tissue. The contact pads are reduced to 4 mm, and the spring tension is reduced to <3 lbs.

Psoriatic mice were selected for use in compound screening based on ear thickness and clinical phenotype. Mice were then randomly assigned to experimental groups.

Week 6–10: Treatment Period (2–4 Weeks)

Administration of experimental compounds (which included antibodies, small molecules, chemicals, viral vectors, drugs) was conducted regularly (once, twice or 3 times per week or daily) for 2–4 weeks at a dose relative to appropriate mg/kg dosages. In general, administration of all compounds were given systemically (SC, IP or IV). Along with the experimental compounds, control groups were run simultaneously with injections of PBS, a negative control (isotype control), and a positive control (anti-IL-12, anti-TNF$\alpha$, corticosteroids, or other known compounds that result in the resolution of psoriatic lesions).

Mice were observed and data recorded for ear thickness and total body weight on a weekly basis. Body weight was monitored to help monitor the overall health of the animal, e.g. exclude viral infection and colitis.

Week 8–12: Evaluation Period (1–2 Weeks After Last Injection of Experimental Compound)

After the completion of treatment period with the experimental compounds, including positive and negative controls a period of at least one or two weeks was allowed to pass to confirm that the drug did or did not have an effect on the severity of disease. Thus the time from the first injection to the end of this waiting period was generally 3–4 weeks in all experiments. At the end of this period, mice were sacrificed, biopsies from both ears taken, and 6 cross sections were made, stained (H and E) and evaluated in blind fashion by at least 2 investigators (given histology score ranged 0–4). Biopsies from all other skin areas were occasionally taken as well.

Skin biopsies were taken from the ear by removing the ear entirely by making the cut below the base of the ear. This method was required to make an adequate observation of the organ as possible. From the base of the ear to the tip the tissue tends to become thinner. Often mild disease is easier to detect at the base of the ear. The histology score was determined by evaluating 6 sections (2 cross sections made from the tip, middle and base sections of the ear). Other biopsies are useful to support the data collected from the ear. Such cases included extremely severe clinical cases where hair loss occurs indicating involvement of other regions of skin.

Scid/scid mice engrafted with T cells have been shown in previous studies to come down with some incidence of colitis. It was found in our experiments that this procedure could be used with immunomodulatory co-factors to create organ specific inflammation, e.g. psoriasis, colitis, etc. Because of the immunostimulating properties of bacterial mitogens or bacterial superantigens it was initially tested whether the co-administration of such agents would have a positive effect on the induction of disease with this novel scid/scid transfer model.

Disease induction, severity, and chronicity. Initially the animals were tested to determine the percentage of mice that came down with disease. The experimental data represented in FIGS. 1 and 2 comes from a group of 40 scid/scid mice that received a transfer of CD4+/CD25− T cells as described above. In, brief, naive scid/scid mice were injected sc. with 3–6×10$^5$ CD4$^+$CD25$^-$ cells on day 0, followed by a sc. injection of 20 μg LPS 24 hours later. The mice were then handled with normal husbandry for 4 at which time clinical signs of psoriasis begin appear on the ears in the form of reddened, thickened skin. On week five 50% of the animals were considered diseased (>=25 μm skin thickness). The incidence of disease improved by week 6 to 76%, and reached 96% on week 7. This data is from one experiment and is representative of 6 experiments.

Figure 2B:
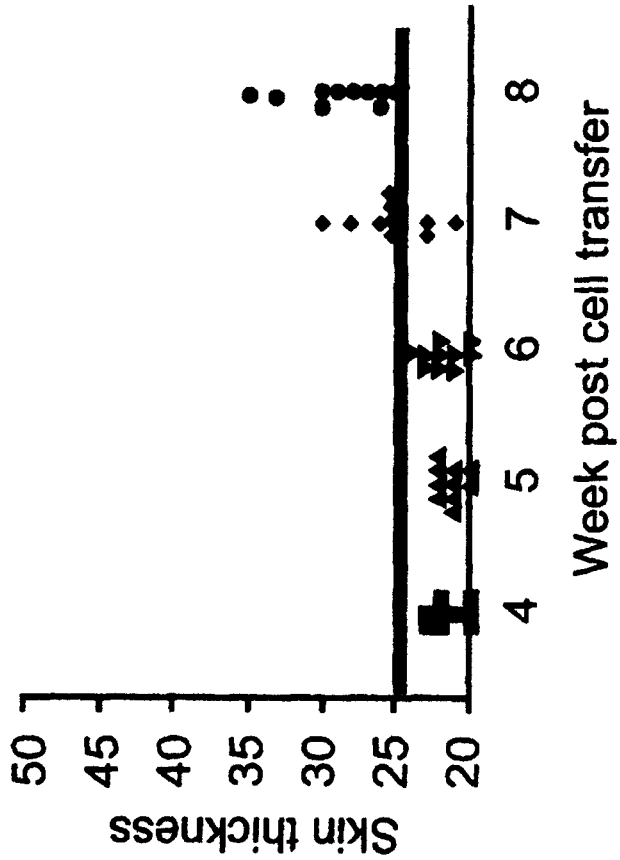

The psoriasis in this model is significant- it does reach high severity. The normal scid/scid mouse skin thickness in the ear is 18–22 μm. As seen in FIG. 1 the distribution of severity attainable in this model has a majority of the mice expressing severe levels of disease (Each mark represents a single ear measurement. n=80. Normal ear thickness: 19–22, Mild disease 25–30 μm. Moderate disease 31–39 μm Severe disease >40 μm). As seen in FIG. 2, the progress of disease can be monitored and the severity of disease is scaleable. The mild to moderately diseased animals are shown to come down with disease (ear thickness becomes >25 μm) between week 7 and 8. In mice that have more severe disease by week 8 will show a more aggressive development of psoriasis and will become disease (develop skin thickness >25 μm) starting on week 5.

Figure 3:
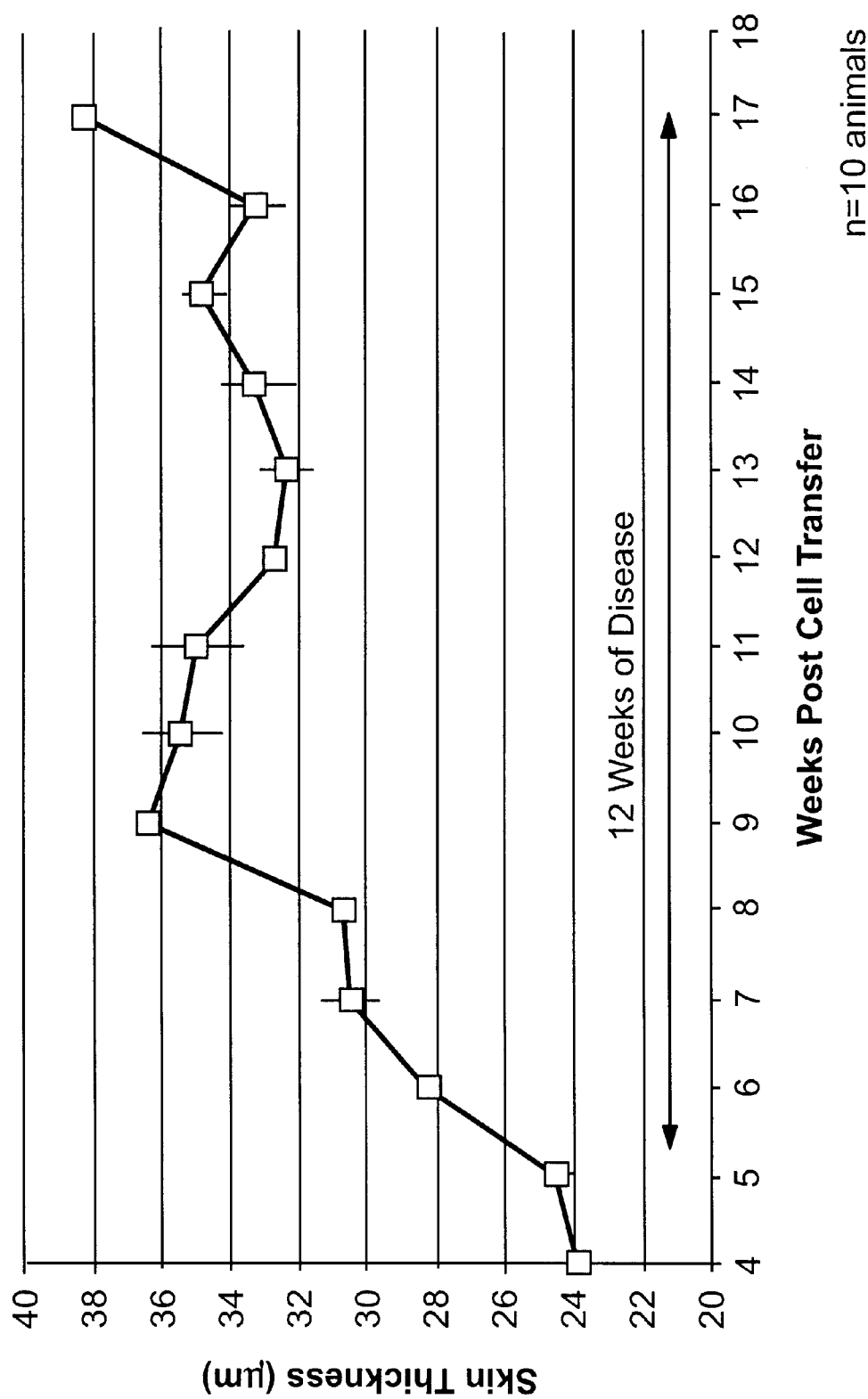
FIG. 3 is a graph demonstrating the chronicity of the induced disease. Error bars=SEM. A group of animals are considered diseased if average ear thickness>25 µm.

In order to determine that this disease was a chronic inflammation, several mice from various experiments were observed for greater than 14 weeks after cell transfer. In FIG. 3 one group of 10 animals which were induced with psoriasis by the standard protocol were observed for 17 weeks after the transfer of T cells. Measurements of the ears of 10 mice were averaged (20 ears in total). In this experiment the average measurement (n=20) was >25 μm on week 5. It was found that the diseased condition not only developed from moderate to severe levels (>30 μm) but also lasted for 12 weeks. This is an adequate time period to demonstrate that the disease does not resolve itself. The chronicity of disease may be attributed to the autoantigens that drive the disease. It is also observed that the severity of the disease is narrow ranged (between 32–36 μm) for a period of 6 weeks (week 9–15). This data was found to be representative of 4 separate experiments.

Figure 4:
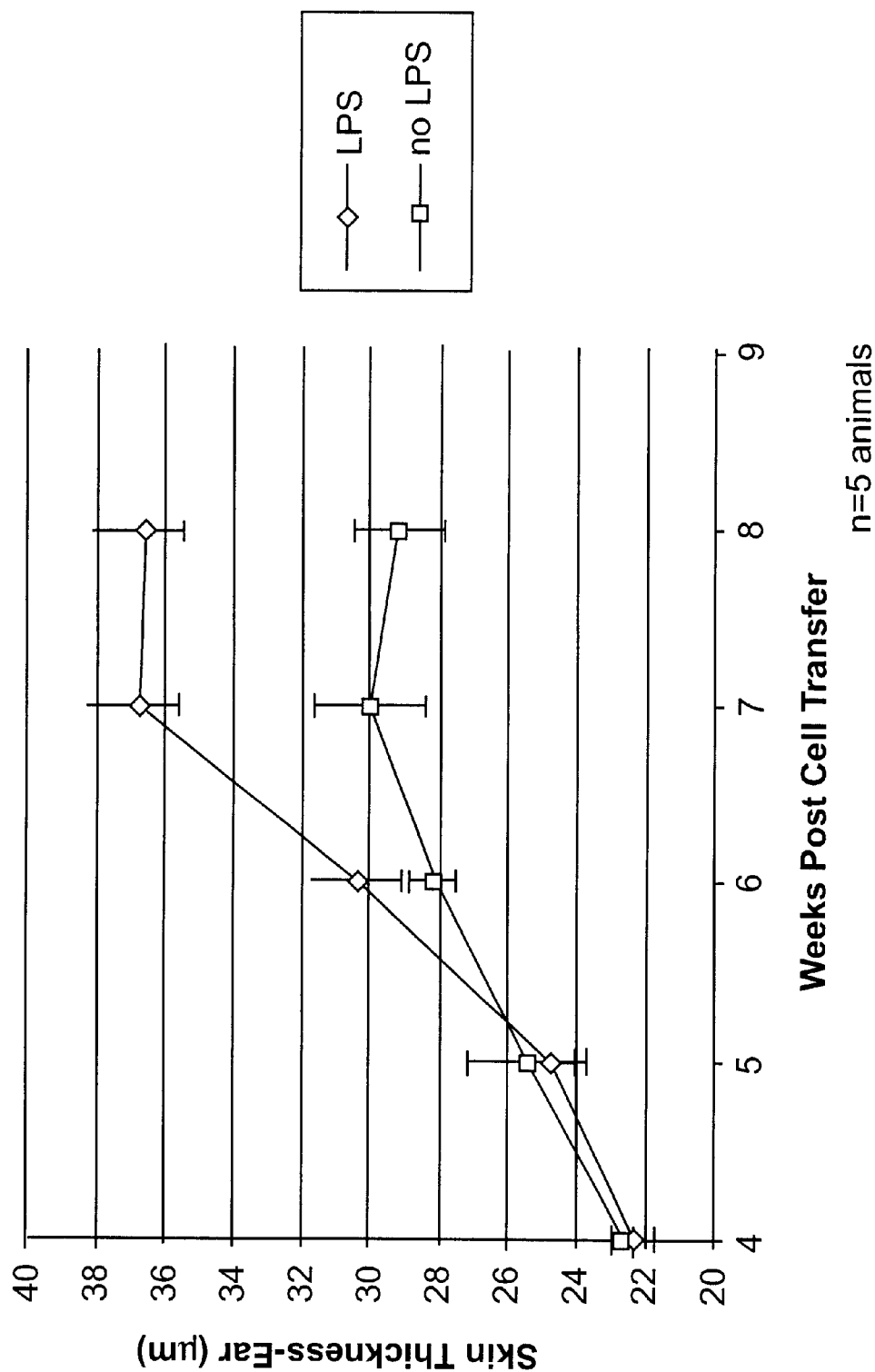
FIG. 4 is a graph illustrating the effects of a co-factor in disease induction. The disease induction protocol was modified to examine animals with and without LPS co-injection.

Co-factor injections are important for their mitogenic properties. In one experiment five mice were compared with the standard induction protocol which included an injection of 20 μg LPS on day one to 5 mice that received the same cells but were not given the injection of LPS. Starting on week 6 the mice that received the LPS displayed a higher severity of psoriasis like disease. By week 7 the mice that received the LPS had an average ear thickness of 36.4 μm +/−0.7 compared to 30 μm+/−1.2 in the mice that did not receive LPS. Both groups of mice had an incidence of disease of 100% (5/5), shown in FIG. 4. Data represents the average of 10 measurements of skin thickness (1 per ear, 2 per mouse n=5 mice), Error bars=SEM. p=3.6×10$^{-3}$ Therefore, the data shows that the use of bacterial antigens results in an increased severity of disease.

The effect of different co-factors on disease induction was assessed. All mice were induced with the same cell population described in the standard protocol. Each group received a single injection of co-factor after cell transfer as follows. No Co-injection: 200 μl PBS s.c on day 1. LPS: 20 μg LPS s.c. diluted in PBS on day 1. LPS+Whole Cells: LPS and 10$^6$ CD25$^-$ cells s.c. on day 14. Viral Vector: 1×10$^6$ viral particles injected s.c. in 200 μl PBS. SEB: 10 μg SEB diluted in 200 μl PBS injected s.c.

The viral vector is the Adenovirus serotype 5 with deletion of E1 and E3 genes. The transgene is the LacZ gene under the control of the cytomegalovirus-IE promoter. The dose (10$^6$ VP) is the virus particle count, not the infections dose (our virus particle dose is equivalent to 10$^5$ TCID 50). The CD25$^-$ cells were selected from Balb/C spleen without other enrichment, and so included all cells including CD8, B, NK cell. The results are shown in FIG. 10. It can be seen that the viral vector co-factor produced a very strong response.

Phenotype of disease inducing cells. The sorted CD4$^+$/CD25$^-$ cell population was tested for purity, by staining with florescein conjugated antibodies against CD4 and CD25 and analysis using a FacsCalibur (Becton Dickenson) and Cell Quest Software. The population was found to stain positively for CD4 and negatively for CD25 on greater than 97% of the cells.

The sorted CD4$^+$/CD25$^-$ cell population was also tested by staining with fluorescein conjugated antibodies against CD45RB. It was found that the disease inducing cells have a heterogeneous phenotype of CD45RB hi and low. Thus, the induction of disease is CD45 independent.

Experiments were also performed demonstrating that secondary transfer of whole spleen cell suspensions from a primary host with disease induced as described above, results in the transfer of disease. Whole spleens from diseased mice (induced by standard protocol) were treated with red blood cell lysing buffer, and reinjected into naive scid/scid mice. Each mouse received 2.5×10$^5$ cells s.c. (n=3).

It was further shown that a suspension of unfractionated spleen cells depleted of CD25 positive cells can be used to induce disease. The host animals were injected with 500,000 splenocytes from normal Balb/C mice, that were depleted of CD25 cells by the same magnetic bead-antibody method described above, in combination with LPS. Cells included in this population, in addition to CD4 T cells, are CD8 T cells, B cells, NK cells, macrophages, dendritic cells etc. The result was an induction of disease.

The general health of the animals with inflammatory disease was monitored not only by daily observations but also by measuring their body weight. In previous studies, the induction of inflammation often involved colitis, which results in a general decrease in health of the animal. We observed three groups of 5 psoriatic mice in each group and found that even after the induction of the inflammatory disease the average weight of the mice stayed very consistent in all groups. In another study 5 psoriatic animals with an average ear thickness starting at 35 μm and increasing to 45 μm (moderate to severe severity) were found to have an average body mass holding between 20–22 mg (normal healthy body mass 19–23 mg) for the entire course of disease progression, and up to 11 weeks post cell transfer. This demonstrates that even severely affected psoriatic mice remain healthy for an extended period of time.

To demonstrate that the disease was not an artifact of the mechanical manipulation of the mice, a study was conducted to show that the transferred cells were the cause of disease. Naive scid/scid mice were given sc. Injections containing 2.5×10$^5$ whole (un-enriched) spleen cells from psoriatic mice that had been induced to develop psoriasis with CD4$^+$/CD25$^-$ cells. All of the test subjects came down with disease (3 out of 3 at week 8). It may be noted that the spleens from diseased scid/scid mice are small. This study shows that the cells transferred in this invention are the cause of disease and that the cells maintain their disease causing properties even after multiple animal transfers.

Figure 7:
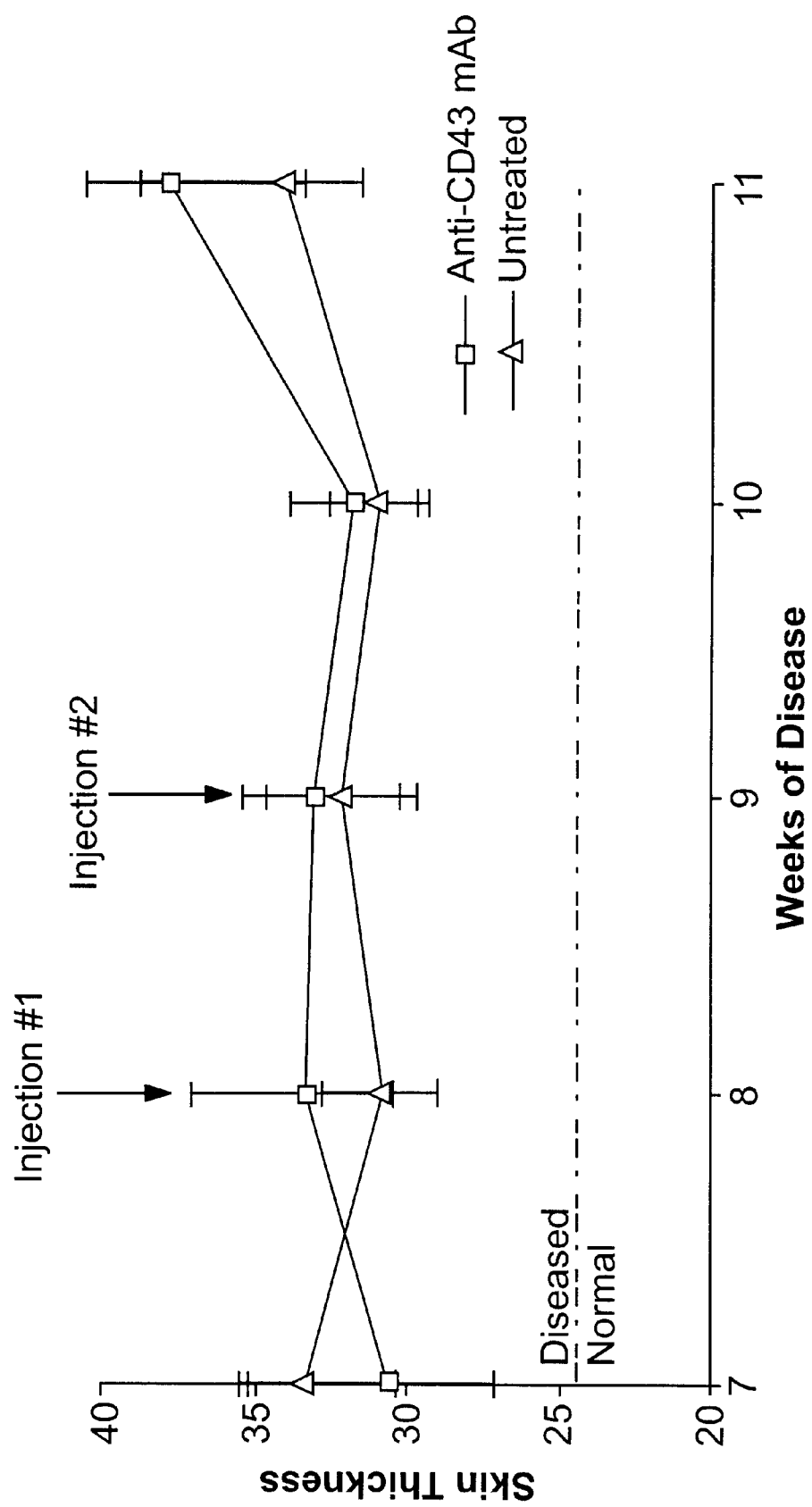
FIG. 7 is a graph depicting the effect of anti-CD43 monoclonal antibody in the inflammation model of the invention.

Administration of anti IL-12 mAb. There have been many examples of the effective anti-inflammatory effect of anti IL-12 mAb treatment. In animal model of the present invention, it was also found to cause a reduction in psoriasis lesions. Animals were tested for the effect of treatment during ongoing psoriatic disease. The disease was induced by the standard protocol, and treatment began on week 9. The treatment with the anti-IL-12 mAb was 1 mg/mouse/week. In the initial experiments (n=5 untreated, n=5 treated) mice received injections of anti-IL-12 mAb at weeks 9 and 10, and were observed for 2 weeks after the final injection. Control animals were left untreated, isotype treated animals received an isotype matched monoclonal antibody against a non mouse antigen. Anti-IL-12 treatment resulted in a skin thickness improvement of −7 $\mu$m compared to an increase in skin thickness of +2 $\mu$m in control isotype treated animals and untreated animals, as shown in FIG. 7.

Figure 5:
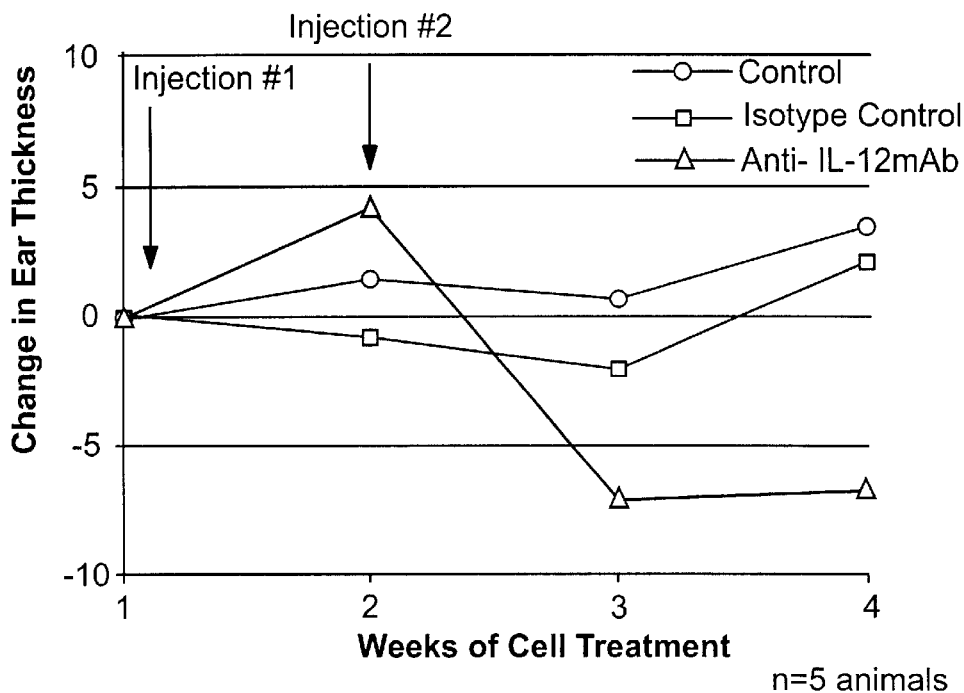
FIG. 5 shows the effects of anti-IL-12 mAb treatment.
Figure 8:
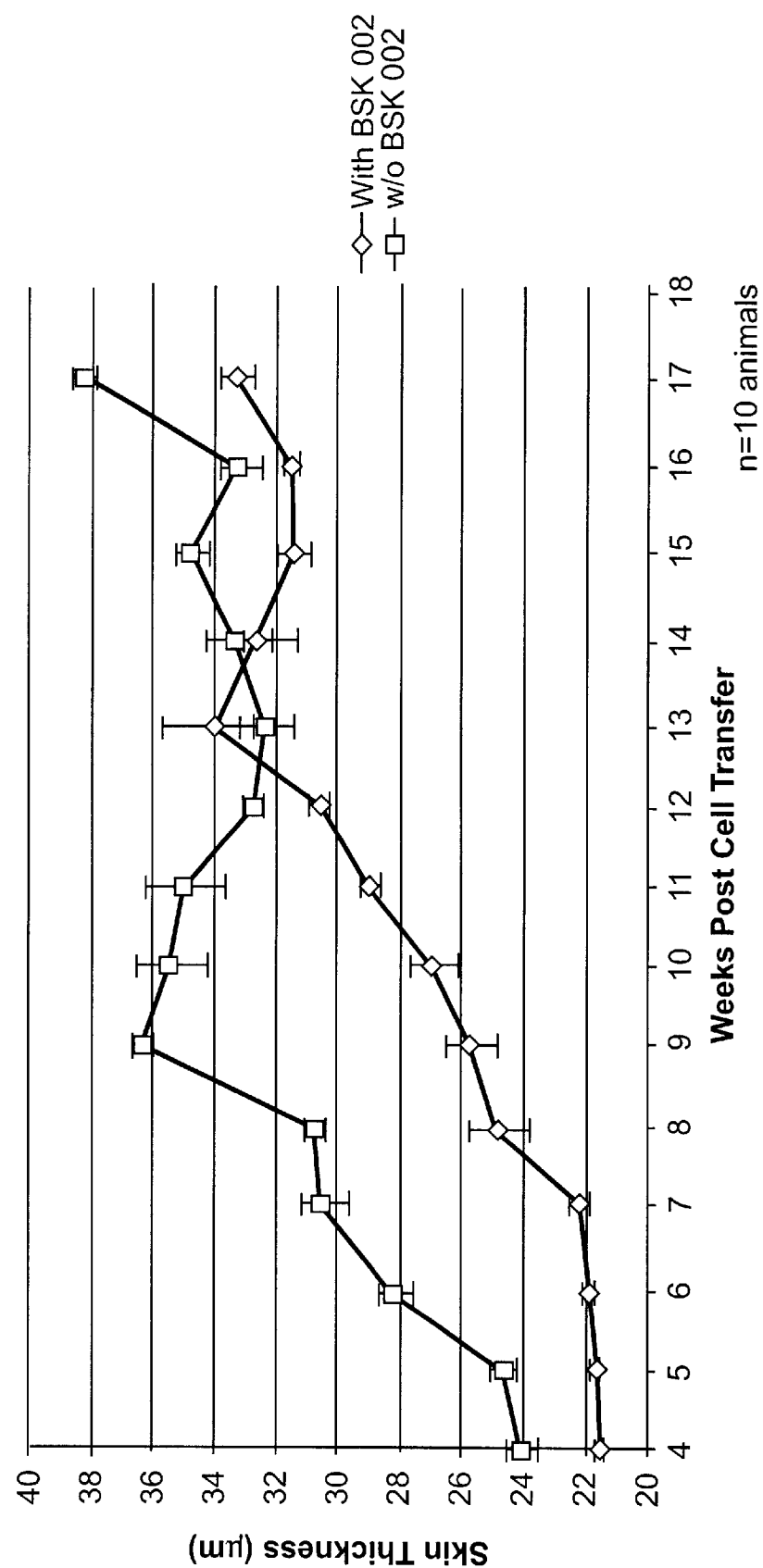
FIG. 8 is a graph depicting the effect of an oral compound on disease progression.

In a separate study, anti IL-12 mAb was used in a positive control group, to determine if an experimental anti-mouse antigen antibody had anti-inflammatory properties. In this experiment there were 5 mice per experimental group: positive control (anti IL-12), negative control (isotype matched anti Human antigen mAb), and the experimental mAb labeled BSK Ab001. At week 12 the animals were sacrificed for histology of the skin tissue. Where the isotype control mice had an average histology score of 2.7 on a scale of 0–4, the anti IL-12 treated mice had a histology score of only 0.5 indicating a nearly complete resolution of psoriatic lesions FIG. 8. Therefore 2 injections of anti-IL-12 were shown to be an effective treatment by clinical observations and by histology, shown in FIG. 5. Treatment began 9 weeks after T cell transfer, injections given on week 1 and 2, all animals received 1 mg/dose. Control animals were left untreated, isotype control animals received an isotype matched monoclonal antibody against a human antigen. p=0.02.

Figure 6:
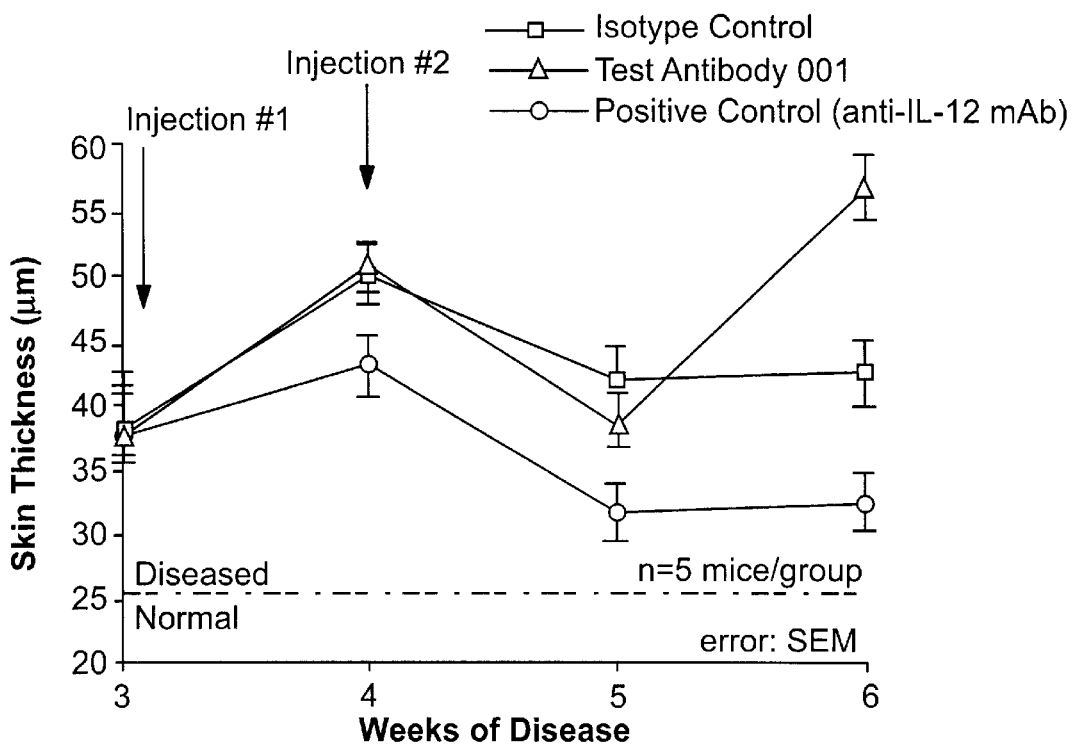
FIG. 6 is a graph depicting antibody screening against the inflammation model of the invention.

An experimental antibody against a mouse antigen (BSK001) was tested, and found to have no effect on psoriasis lesions. The skin thickness on week 5 of disease did not decrease, as shown in FIG. 6. Each group consisted of 5 mice and all were induced with psoriasis by standard protocol. The treatment for each group was 1 mg of antibody per dose: positive control (anti IL-12 mAb), negative control (isotype matched anti-human antigen mAb), and the experimental (mAb labeled BSK Ab001), began on the third week, after disease had begun with moderate to severe psoriasis. Where as the mice in the positive control group demonstrated reduced skin thickness (7 $\mu$m improvement), the experimental mAb BSK Ab001 group of mice had an increase in ear thickness of 19 $\mu$m 2 weeks after the final injection, p=5.0×10$^{-9}$. The isotype negative control mice completed the treatment and observation period (total of 4 weeks) with no change in ear thickness.

These results were confirmed by histology scores composed of the average of histology scores given to each ear of the experimental groups histology. Semiquantitive histological scores from 0 to 4 were given based on the severity of inflammation. Initial histological evaluation was performed by an independent outside pathologist. In later studies evaluation was blindly conducted by three different investigators. 0=no signs of inflammation; 1=very low focal areas of infiltration, mild acanthosis; 2=low level of mononuclear cell infiltration, mild thickening of epidermis, mild to moderate acanthosis 3=high level of mononuclear cell infiltration, high vascular density, thickening of the epidermis (acanthosis, rete pegs and hyperplasia of epidermis and keratinocytes, microabscesses, thinning of the granular cell layer 4=very extensive infiltration in epidermis and dermis, very high vascular density, extreme thickening of epidermis, pustule formation and destruction of granular cell layers.

In another study, it was found that treatment with anti CD43 mAb showed no effect on the progression of disease (see FIG. 7). In this experiment all mice were induced with disease by standard protocol. Five mice per group were utilized to compare the affects of anti-CD43 to untreated mice. The treated group received a treatment regimen of 2 injections on week 7 and 8, of 1 mg per mouse mAb given sc. The mice were observed for 2 weeks after the final injection and no significant differences between the groups were found as observed by ear thickness. Anti CD43 was selected as a possible therapeutic mAb due to previous studies that showed this antibody has the ability to abrogate semi-chronic diseases and to prevent the induction of disease. Due to the lack of improvement in disease severity in our model we determined that anti CD43 mAb is not an effective treatment in truly chronic disease models. From this we show that the model is selective and does not react to all antibodies against mouse antigens.

Animals were tested to compare the effect of an experimental oral compound (BSK 002) on the induction and severity of psoriatic disease. Twenty animals were induced with psoriasis by the standard protocol and were divided into 2 groups: autoclaved water treated with BSK 002, and normal autoclaved water. The effect of compound BSK002 was compared to a negative control at week 4, and it was found that 33% (3/9) of animals without BSK 002 compared to 0% (0/10) mice with BSK002 showed a disease state (ear thickness >=25 $\mu$m). At week nine, while both groups had diseased animals, the group without BSK002 administration developed a higher severity (30 $\mu$m vs 24 $\mu$m) as well as higher penetrance 100% (9/9) compared to 50% (5/10). Hence the presence of the experimental compound BSK002 slows down the onset of psoriasis and reduces both penetrance and severity (shown in FIG. 8). On week 11 all animals had disease (100%; 10/10) in the normal water group while the treated water group had 80% (8/10). At week 9: p=1.7×10$^{-5}$, week 11: p=3.4×10$^{-2}$, week 17: p=4.3×10$^{-2}$.

Figure 9:
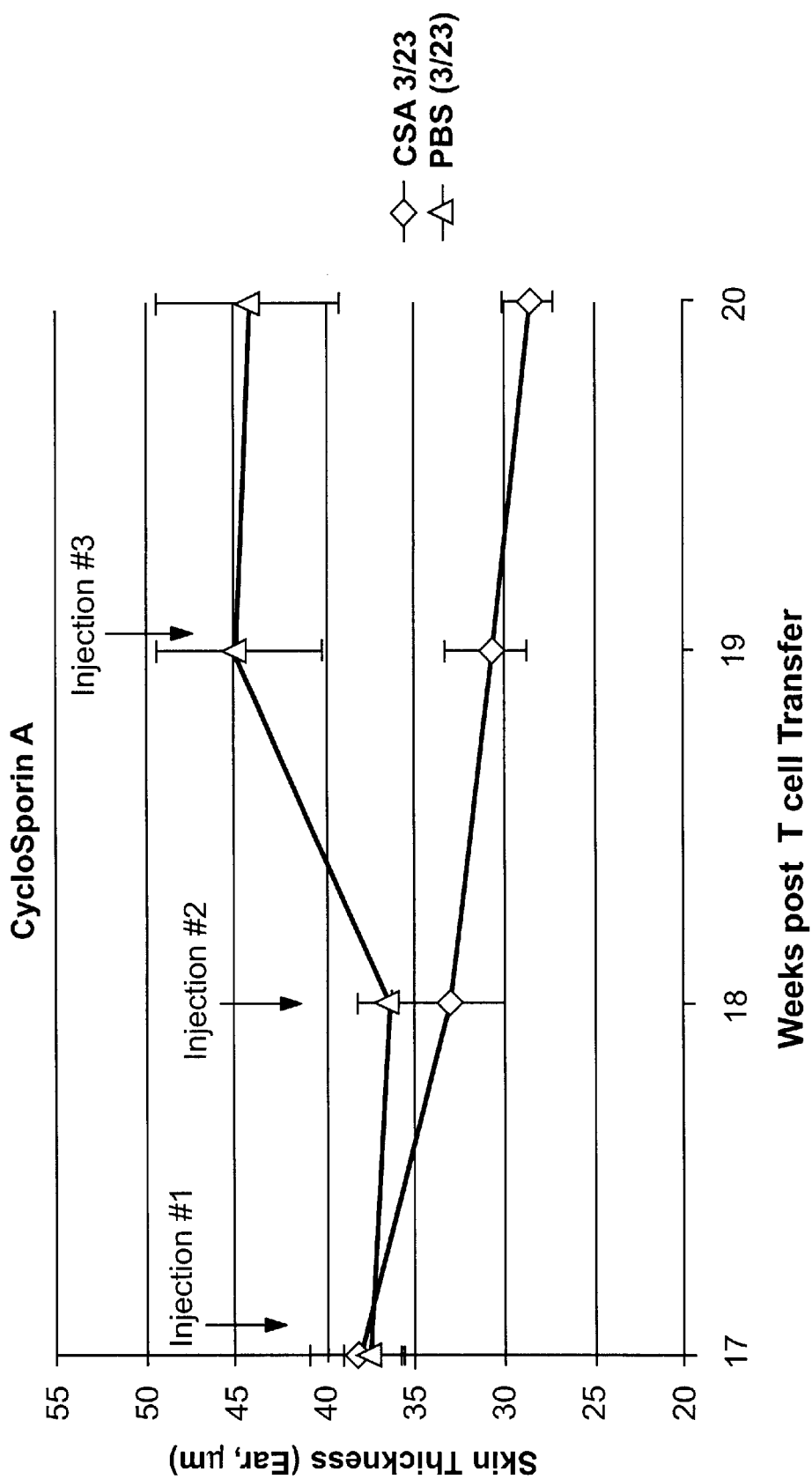
FIG. 9 shows the effect of cyclosporin on disease progression.

Animals were tested to determine the effect of cyclosporin A on the development of disease (shown in FIG. 9), with injections of the compound at 17, 18 and 19 weeks post-T cell transfer. It was found that the presence of the cyclosporin A reduced the severity of the disease, p=3.6×10$^{-2}$.

The known immunosuppressant methylprednisone was also found to control the disease. After injection with methylprednisone, at a dose of 40 mg/kg twice/day for 8 days, the ear thickness improved immediately compared to the control animals which received injections of PBS. After 8 days of treatment the skin thickness was reduced from 33.7 to 22.4 $\mu$m p=2.01×10$^{-6}$ To demonstrate that the disease could be induced at a site other than skin, a study was conducted in which CD25 negative effector cells were transferred into scid/scid mice without co-injection into the skin. Food and gut flora are acting as co-factor antigen(s) in this model set-up. After, 6–8 weeks animals developed severe colitis as measured by weight (average weight 15.8+/−0.6 (n=4), Normal weight is 19–23).

What is claimed is:

1. A panel for compound testing, comprising immunodeficient rodents comprising exogenous immunocompetent $CD4^+$ T cells, wherein said T cells were depleted of cells expressing CD25 prior to introduction into said rodent;

antigen presenting cells to which said T cells are tolerant, wherein said antigen presenting cells initiate an inflammatory response by said T cells; and chronically inflamed tissue as a result of said inflammatory response, wherein at least one of said mammals comprises a known immunomodulatory compound, and at least one of said immunodeficient rodents comprises a test compound suspected of immunomodulatory activity.

2. A method for screening a candidate therapy for efficacy in treatment of chronic inflammation, the method comprising:

transferring a cell population comprising immunocompetent $CD4^+$ T cells and lacking CD25 positive T cells, from a donor rodent to an allogeneic immunocompromised rodent host, wherein said immunocompetent T cell population is tolerant of the host major histocompatibility antigens but is immunoreactive with one or more antigens present in said host;

wherein said host develops chronic inflammation, said chronic inflammation including mononuclear cell infiltration and high vascular density;

treating said rodent host with said candidate therapy;

determining the severity of disease in the presence of said therapy, wherein a decrease in severity of disease in the treated rodent host relative to control rodent host is indicative of efficacy in treatment.

3. The method according to claim 2, wherein the method further comprises administering an immunostimulant to a localized site in said rodent host.

4. The method according to claim 2, wherein said $CD4^+$ T cells are reactive to minor histocompatibility antigens present in said host.

5. The method according to claim 2, wherein said candidate therapy comprises administration of one or a combination of candidate immunosuppressant drugs.

6. The method according to claim 2, further comprising a comparison of severity of said disease to a positive control animal treated with a known immunomodulatory compound.

7. The method of claim 2, wherein said donor rodent and said rodent host are mice.

8. The method of claim 7 wherein the donor mouse and host mouse are MHC matched.

9. The method of claim 7, wherein said host mouse is a scid-scid mouse.

10. The method according to claim 3, wherein said immunostimulant is a polyclonal activating endotoxin.

11. The method according to claim 2, wherein said cell population comprising immunocompetent $CD4^+$ T cells and lacking CD25 positive T cells is an isolated population of $CD4^+$ T cells.

12. The method according to claim 2, wherein said cell population comprising immunocompetent $CD4^+$ T cells and lacking CD25 positive T cells are a population of splenocytes depleted only of $CD25^+$ cells.

* * * * *